United States Patent
Tran et al.

(10) Patent No.: US 11,383,068 B2
(45) Date of Patent: Jul. 12, 2022

(54) NEUROVASCULAR DISTAL ACCESS SUPPORT CATHETERS, ASPIRATION CATHETERS, OR DEVICE SHAFTS

(71) Applicant: eLum Technologies, Inc., Fremont, CA (US)

(72) Inventors: Quang Tran, Atherton, CA (US); Noelle Bagnall, Irvine, CA (US); Victor Barajas, Pleasanton, CA (US)

(73) Assignee: eLum Technologies, Inc., Fremont, CA (US)

( * ) Notice: Subject to any disclaimer, the term of this patent is extended or adjusted under 35 U.S.C. 154(b) by 92 days.

(21) Appl. No.: 16/506,694

(22) Filed: Jul. 9, 2019

(65) Prior Publication Data
US 2020/0023164 A1    Jan. 23, 2020

Related U.S. Application Data

(60) Provisional application No. 62/858,835, filed on Jun. 7, 2019, provisional application No. 62/701,254, filed on Jul. 20, 2018.

(51) Int. Cl.
| | | |
|---|---|---|
| *A61M 25/01* | (2006.01) | |
| *A61M 25/00* | (2006.01) | |
| *A61M 1/00* | (2006.01) | |
| *A61M 25/09* | (2006.01) | |

(52) U.S. Cl.
CPC .... *A61M 25/0138* (2013.01); *A61M 25/0054* (2013.01); *A61M 1/0023* (2013.01); *A61M 25/0053* (2013.01); *A61M 2025/091* (2013.01)

(58) Field of Classification Search
CPC .......... A61M 25/0138; A61M 25/0054; A61M 1/0023; A61M 2025/091; A61M 25/0053; A61M 1/008; A61M 25/0045; A61M 25/0051; A61M 2025/0681; A61M 25/0015; A61M 2025/0042; A61B 17/221
See application file for complete search history.

(56) References Cited

U.S. PATENT DOCUMENTS

| | | | |
|---|---|---|---|
| 5,827,304 A | | 10/1998 | Hart |
| 5,906,627 A | * | 5/1999 | Spaulding ...... A61B 17/320783 |
| | | | 606/159 |
| 6,066,158 A | | 5/2000 | Engelson et al. |

(Continued)

FOREIGN PATENT DOCUMENTS

| | | |
|---|---|---|
| AT | 404123 | 8/2008 |
| EP | 1030603 | 8/2000 |

(Continued)

*Primary Examiner* — Nathan R Price
*Assistant Examiner* — Anh Bui
(74) *Attorney, Agent, or Firm* — Kilpatrick Townsend & Stockton LLP

(57) ABSTRACT

A catheter or shaft, such as a distal access support or aspiration catheter, is provided that is configured to be advanced at least partially within a patient. The catheter or shaft may include a flexible and hollow shaft including a proximal end and a distal end. The flexible and hollow shaft may include a slotted portion with a plurality of slotted openings, the slotted portion including a first segment with a first pattern of slotted openings and a second segment extending proximally relative the first segment with a second pattern of slotted openings different from the first pattern.

31 Claims, 10 Drawing Sheets

(56) References Cited

U.S. PATENT DOCUMENTS

| | | |
|---|---|---|
| 6,168,579 B1 | 1/2001 | Tsugita et al. |
| 6,221,006 B1 | 4/2001 | Dubrul et al. |
| 6,238,412 B1 | 5/2001 | Dubrul et al. |
| 6,254,571 B1 | 7/2001 | Hart |
| 6,258,115 B1 | 7/2001 | Dubrul et al. |
| 6,273,876 B1 | 8/2001 | Klima et al. |
| 6,511,897 B2 | 1/2003 | Arima et al. |
| 6,530,939 B1 | 3/2003 | Hopkins et al. |
| 6,589,263 B1 | 7/2003 | Hopkins et al. |
| 6,685,722 B1 | 2/2004 | Rosenbluth et al. |
| 6,699,260 B2 | 3/2004 | Dubrul et al. |
| 6,712,835 B2 | 3/2004 | Mazzocchi et al. |
| 6,755,847 B2 | 6/2004 | Eskuri et al. |
| 6,878,151 B2 | 4/2005 | Carrison et al. |
| 7,232,432 B2 | 6/2007 | Fulton et al. |
| 7,320,698 B2 | 1/2008 | Eskuri et al. |
| 7,331,980 B2 | 2/2008 | Dubrul et al. |
| 7,691,121 B2 | 4/2010 | Rosenbluth et al. |
| 7,780,696 B2 | 8/2010 | Daniel et al. |
| 7,905,896 B2 | 3/2011 | Straub et al. |
| 8,100,935 B2 | 1/2012 | Rosenbluth et al. |
| 8,109,962 B2 | 2/2012 | Pal |
| 8,317,251 B2 | 11/2012 | Nelson |
| 8,317,748 B2 | 11/2012 | Fiorella et al. |
| 8,357,178 B2 | 1/2013 | Pedersen et al. |
| 8,512,352 B2 | 8/2013 | Martin et al. |
| 8,535,334 B2 | 9/2013 | Martin et al. |
| 8,545,526 B2 | 10/2013 | Martin et al. |
| 8,696,622 B2 | 4/2014 | Fiorella et al. |
| 8,728,116 B1 * | 5/2014 | Janardhan .......... A61M 25/0023 606/200 |
| 8,777,976 B2 | 7/2014 | Brady et al. |
| 8,784,441 B2 | 7/2014 | Rosenbluth et al. |
| 8,795,305 B2 | 8/2014 | Martin et al. |
| 8,795,345 B2 | 8/2014 | Pedersen et al. |
| 8,801,748 B2 | 8/2014 | Martin et al. |
| 8,852,205 B2 | 10/2014 | Gilvarry et al. |
| 8,852,226 B2 | 10/2014 | Gilson et al. |
| 8,932,319 B2 | 1/2015 | Martin et al. |
| 8,945,143 B2 | 2/2015 | Cragg et al. |
| 8,979,157 B2 | 3/2015 | Nelson |
| 9,186,487 B2 | 11/2015 | Dubrul et al. |
| 9,204,887 B2 | 12/2015 | Cully et al. |
| 9,254,371 B2 | 2/2016 | Martin et al. |
| 9,271,747 B2 | 3/2016 | Martin |
| 9,271,748 B2 | 3/2016 | Martin |
| 9,308,016 B2 | 4/2016 | Escudero et al. |
| 9,358,094 B2 | 6/2016 | Martin et al. |
| 9,427,252 B2 | 8/2016 | Sos |
| 9,439,664 B2 | 9/2016 | Sos et al. |
| 9,456,834 B2 | 10/2016 | Folk et al. |
| 9,498,604 B2 | 11/2016 | Dubrul et al. |
| 9,597,101 B2 | 3/2017 | Galdonik et al. |
| 9,642,639 B2 | 5/2017 | Brady et al. |
| 9,717,514 B2 | 8/2017 | Martin et al. |
| 9,833,253 B1 | 12/2017 | Ulm |
| 9,848,906 B1 | 12/2017 | Eskridge |
| 9,943,323 B2 | 4/2018 | Martin et al. |
| 10,064,635 B2 | 9/2018 | Martin et al. |
| 10,076,346 B2 | 9/2018 | Martin |
| 10,172,633 B2 | 1/2019 | Martin et al. |
| 2002/0026211 A1 | 2/2002 | Khosravi et al. |
| 2003/0144686 A1 | 7/2003 | Martinez et al. |
| 2004/0020492 A1 | 2/2004 | Dubrul et al. |
| 2004/0098033 A1 * | 5/2004 | Leeflang .................. A61F 2/014 606/200 |
| 2004/0133232 A1 | 7/2004 | Rosenbluth et al. |
| 2004/0199202 A1 | 10/2004 | Dubrul et al. |
| 2004/0260332 A1 | 12/2004 | Dubrul et al. |
| 2004/0260333 A1 | 12/2004 | Dubrul et al. |
| 2005/0090857 A1 | 4/2005 | Kusleika et al. |
| 2005/0177132 A1 * | 8/2005 | Lentz ................ A61M 25/0013 604/525 |
| 2005/0288656 A1 * | 12/2005 | Koerner ............ A61M 25/0043 606/21 |
| 2007/0191876 A1 | 8/2007 | Dubrul et al. |
| 2007/0288054 A1 | 12/2007 | Tanaka et al. |
| 2008/0147170 A1 | 6/2008 | Vrba |
| 2008/0188793 A1 * | 8/2008 | Kozak .............. A61B 17/32037 604/22 |
| 2009/0069828 A1 | 3/2009 | Martin et al. |
| 2010/0030256 A1 | 2/2010 | Dubrul et al. |
| 2010/0114113 A1 | 5/2010 | Dubrul et al. |
| 2011/0009942 A1 | 1/2011 | Gregorich et al. |
| 2011/0175391 A1 | 7/2011 | Nelson |
| 2011/0213403 A1 | 9/2011 | Aboytes |
| 2013/0345739 A1 | 12/2013 | Brady et al. |
| 2014/0031856 A1 | 1/2014 | Martin et al. |
| 2014/0058324 A1 | 2/2014 | Salahieh et al. |
| 2014/0236219 A1 | 8/2014 | Dubrul et al. |
| 2014/0260928 A1 | 9/2014 | Janardhan et al. |
| 2014/0371781 A1 | 12/2014 | Morgan |
| 2015/0018929 A1 | 1/2015 | Martin et al. |
| 2015/0127035 A1 | 5/2015 | Vonesh et al. |
| 2015/0209058 A1 | 7/2015 | Ferrera et al. |
| 2015/0238207 A1 | 8/2015 | Cox et al. |
| 2016/0022293 A1 | 1/2016 | Dubrul et al. |
| 2016/0096004 A1 * | 4/2016 | Gerrans ................ A61B 1/045 600/112 |
| 2016/0220346 A1 | 8/2016 | Bonnette et al. |
| 2016/0367285 A1 | 12/2016 | Sos |
| 2017/0325830 A1 | 11/2017 | Martin et al. |
| 2017/0333675 A1 * | 11/2017 | Cottone ............ A61M 25/0045 |
| 2018/0161185 A1 | 6/2018 | Kresslein et al. |
| 2018/0221037 A1 | 8/2018 | Martin et al. |
| 2018/0368865 A1 | 12/2018 | Martin et al. |
| 2019/0015121 A1 | 1/2019 | Martin |

FOREIGN PATENT DOCUMENTS

| | | |
|---|---|---|
| EP | 1617893 | 1/2006 |
| JP | 4731471 | 4/2011 |
| JP | 2011136180 | 7/2011 |
| WO | 9923952 | 5/1999 |
| WO | 2004093966 | 11/2004 |
| WO | 2017117092 | 7/2017 |
| WO | 2018043279 | 3/2018 |

\* cited by examiner

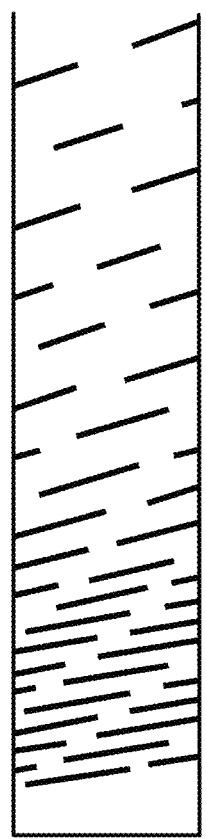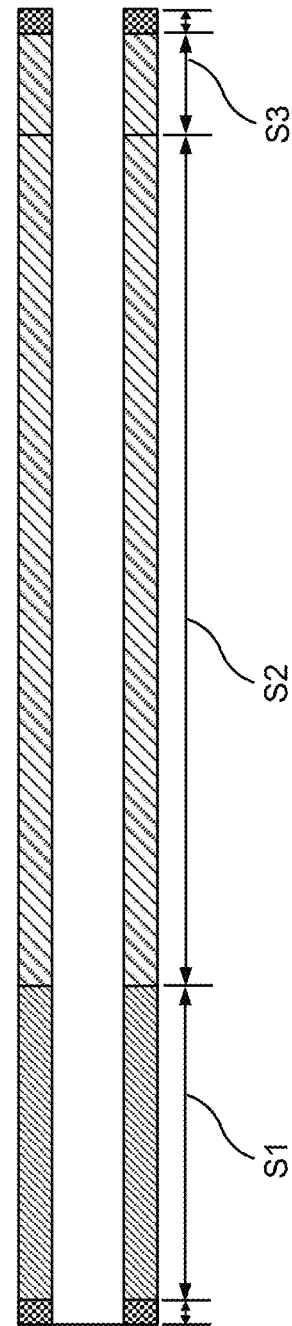
FIG. 1J
FIG. 1K

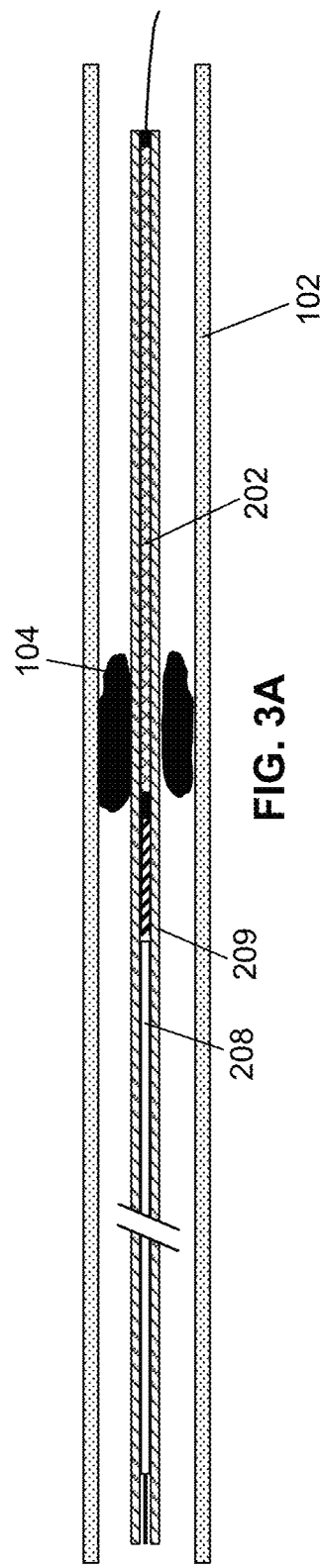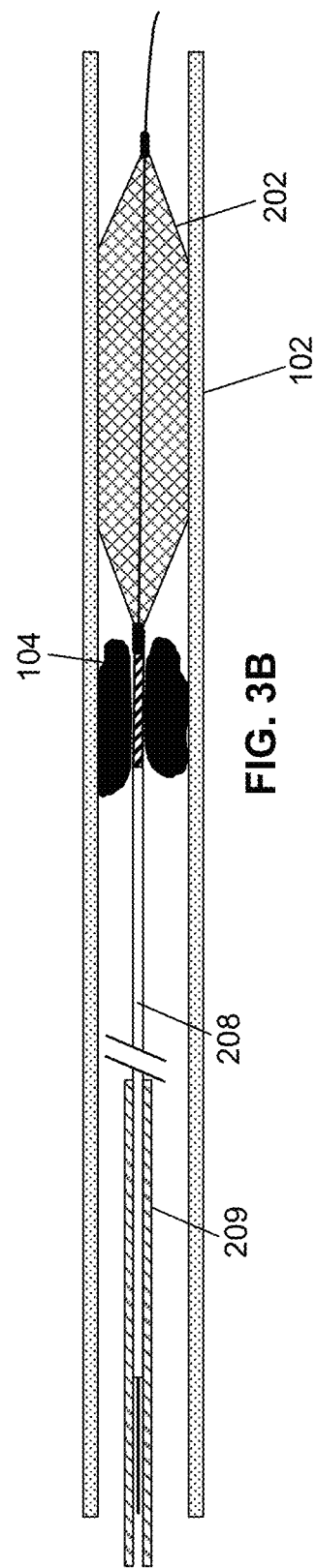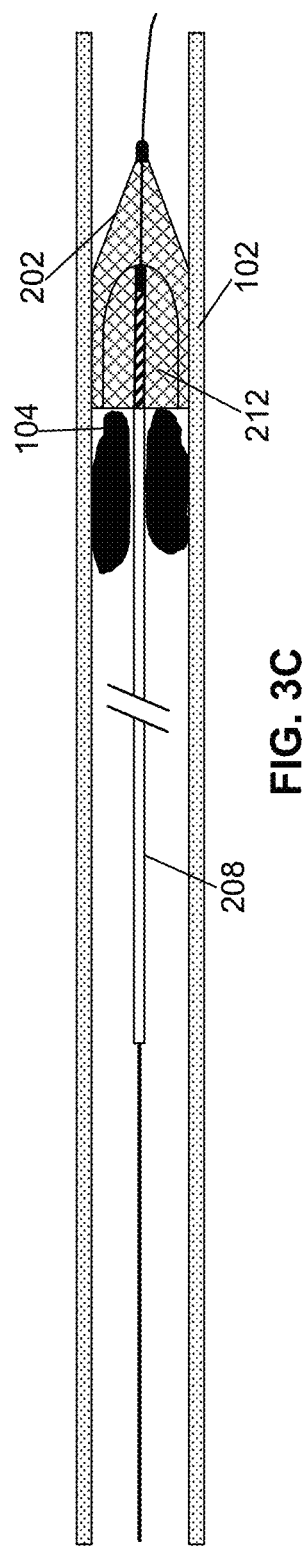

500a

502a — Advanced a distal access support catheter into a patient. The distal access support catheter includes a flexible and hollow shaft including a proximal end and a distal end. The shaft includes a slotted portion with a plurality of slotted openings and the slotted portion includes a first segment with a first pattern of slotted openings and a second segment extending proximally relative to the first segment with a second pattern of slotted openings different from the first pattern.

504a — Bending the slotted portion of the shaft in at least two spaced apart locations while advancing the catheter through the vasculature of the patient.

502b — Advancing an aspiration catheter into a patient distally of an obstruction. The catheter includes a flexible and hollow shaft including a proximal end and a distal end. The shaft includes a slotted portion with a plurality of slotted openings and the slotted portion includes a first segment with a first pattern of slotted openings and a second segment extending proximally relative to the first segment with a second pattern of slotted openings different from the first pattern.

504b — Bending the slotted portion of the shaft in at least two spaced apart locations while advancing the catheter through the vasculature of the patient.

506b — Aspirating the obstruction out of the patient through the shaft.

FIG. 5B

NEUROVASCULAR DISTAL ACCESS SUPPORT CATHETERS, ASPIRATION CATHETERS, OR DEVICE SHAFTS

CROSS REFERENCE TO RELATED APPLICATION DATA

The present application claims the benefit under 35 USC § 119(e) of U.S. Provisional Appln. Nos. 62/701,254 filed Jul. 20, 2018 and 62/858,835 filed Jun. 7, 2019; the full disclosures which are incorporated herein by reference in their entirety for all purposes.

BACKGROUND OF THE INVENTION

This application relates generally to catheters for use in medical applications, and more specifically relates to neurovascular distal access support catheters, intravascular-device shafts, and/or aspiration catheters and methods of use or manufacture.

Typically, catheters may be used for a variety of medical applications. For example, catheters may be designed as delivery catheters configured to position medical devices within a patient directly or indirectly (e.g., via one or more intermediary catheters). Such catheters may also be coupled to a fluid source to deliver fluid to a designated location within a patient or to inflate a medical device (e.g., a balloon). Catheters may be coupled to an aspiration source to aspirate (e.g., obstructions) trapped within a patient. Catheters may be required to navigate particularly narrow or small diameter, tortuous, or curved vasculature to be advanced into a desired position within a patient. Constructing braided or coiled catheters with additional materials or materials with different stiffness may provide flexibility as needed to navigate particularly tortuous vasculature. However, the additional materials may also lead to an increase in overall size or wall thickness of such catheters. Therefore, it would be desirable to provide improved catheters, and in particular, distal access support and/or aspiration catheters with improved features including increased flexibility or improved sizing (e.g., increased inner diameter or decreased wall thickness or outer diameter while maintaining sufficient structural integrity.

BRIEF SUMMARY OF THE INVENTION

According to an aspect of the invention, a catheter or shaft (e.g., a distal access support catheter, an aspiration catheter, an intravascular-device shaft) configured to be advanced at least partially within a patient is provided that includes a flexible and hollow shaft including a proximal end and a distal end, the flexible and hollow shaft including a slotted portion with a plurality of slotted openings. The slotted portion includes a first segment with a first pattern of slotted openings and a second segment extending proximally relative the first segment with a second pattern of slotted openings different from the first pattern.

In some embodiments, first pattern of slotted openings includes a repeating helical pattern of cut and uncut portions extending circumferentially around and along a length of the first segment and wherein the second pattern of slotted openings includes a repeating helical pattern of cut and uncut portions extending circumferentially around and along a length of the second segment.

In some embodiments, a longitudinal spacing between the slotted openings of the first pattern at a distal portion of the first segment is smaller relative to a longitudinal spacing between the slotted openings of the second pattern at a proximal portion of the second segment such that a density of the slotted openings at the distal portion is greater relative to a density of the slotted openings at the proximal portion. In some embodiments, the helical pattern of cut and uncut portions of the first or second patterns of slotted openings extend circumferentially around and along a length of the first or second segments and alternates between cut and uncut portions such that uncut portions extend between two cut portions. In some embodiments, a combined arc length of circumferentially adjacent cut and uncut portions of the helical pattern of the first pattern or second pattern of slotted openings is between 100 degrees and 180 degrees.

In certain embodiments, the distal end of the flexible and hollow shaft is coupled to an intravascular device that includes an expandable basket movable between a collapsed configuration and an expanded configuration, the expandable basket configured to be in the collapsed configuration during delivery into a vasculature of the patient via the flexible and hollow shaft of the catheter or shaft and in the expanded configuration during engagement and retrieval of an obstruction. The expandable basket includes a proximal end and a distal end, wherein at least one of the proximal end or the distal end is movable relative to each other such that a proximal portion of the expandable basket is invertible towards a distal portion of the expandable basket to form a proximally oriented cavity in the expanded configuration. In certain embodiments, the distal end of the flexible and hollow shaft is coupled to a flow diverter configured to be delivered into a patient's vasculature. In other embodiments, the distal end of the flexible and hollow shaft is coupled to a coil embolization device configured to be delivered into a patient's vasculature.

In some embodiments, the flexible and hollow shaft is sized and adapted to allow aspiration of an obstruction through the flexible and hollow shaft. In other embodiments, the flexible and hollow shaft is sized and adapted to allow a delivery catheter for an intravascular device to extend therethrough, the delivery catheter configured to position the intravascular device distally of the distal end of the distal access support catheter. In yet other embodiments, the slotted portion is configured to provide the flexible and hollow shaft with flexibility to traverse at least two bends having angles of at least or up to 90 degrees during advancement through the patient. In further embodiments, the slotted portion is configured to provide the flexible and hollow shaft with flexibility to traverse at least three bends up having angles of at least or up to 90 degrees during advancement through the patient.

In some embodiments, a ratio of an area of the slotted portion of the flexible and hollow shaft without slotted openings relative to an area of the slotted portion with slotted openings has a value up to 50%. In some embodiments, the ratio may be greater than 50%. The slotted openings may be laser-cut. The flexible and hollow shaft may be formed out of a hypotube. The flexible and hollow shaft may include at least one of a non-slotted portion extending proximally relative the slotted portion or a non-slotted portion extending distally relative the slotted portion. The flexible and hollow shaft may be constructed out of one or more of stainless steel, nitinol, chromium, cobalt, platinum, or polymer. In some embodiments, the flexible and hollow shaft is operably coupled to or in fluid communication with one or more of a catheter control handle, aspiration source, inflation source, or fluid delivery source.

In some embodiments, the flexible and hollow shaft does not include a coil or braided material. The catheter may include an outer liner extending coaxially around the flexible and hollow shaft. In certain embodiments, the flexible and hollow shaft does not include an inner liner extending coaxially within the flexible and hollow shaft. The outer liner may have a uniform hardness along its length. In some embodiments, an inner liner extending coaxially within the flexible and hollow shaft such that the flexible and hollow shaft is sandwiched between the inner and outer liners. In some embodiments, the inner liner is directly coupled to the flexible and hollow shaft.

According to another aspect of the invention, an aspiration catheter configured to be advanced at least partially within a patient proximate to an obstruction to aspirate the obstruction therefrom is provided that includes a flexible and hollow shaft including a proximal end and a distal end, the flexible and hollow shaft including a slotted portion with a plurality of slotted openings, wherein the slotted portion includes a first segment with a first pattern of slotted openings and a second segment extending proximally relative the first segment with a second pattern of slotted openings different from the first pattern.

In some embodiments, the first pattern of slotted openings includes a repeating helical pattern of cut and uncut portions extending circumferentially around and along a length of the first segment and wherein the second pattern of slotted openings includes a repeating helical pattern of cut and uncut portions extending circumferentially around and along a length of the second segment.

In some embodiments, a longitudinal spacing between the slotted openings of the first pattern at a distal portion of the first segment is smaller relative to a longitudinal spacing between the slotted openings of the second pattern at a proximal portion of the second segment such that a density of the slotted openings at the distal portion is greater relative to a density of the slotted openings at the proximal portion. In some embodiments, the longitudinal spacing of the first and/or second segment progressively may vary along the length of the first and/or second segment (or along the length of the catheter or shaft). In some embodiments, the helical pattern of cut and uncut portions of the first or second patterns of slotted openings extend circumferentially around and along a length of the first or second segments and alternates between cut and uncut portions such that uncut portions extend between two cut portions. In some embodiments, a combined arc length of circumferentially adjacent cut and uncut portions of the helical pattern of the first pattern or second pattern of slotted openings is between 100 degrees and 180 degrees. In some embodiments, a ratio of an arc length of a cut portion to an arc length of an uncut portion may progressively vary along the length of the first and/or second segment (or along the length of the catheter or shaft). As an example, the ratio may progressively decrease along the length of the first and/or second segment. In some embodiments, the longitudinal spacing of the first and/or second segment may progressively vary along the length of the first and/or segment, and the ratio of an arc length of a cut portion to an arc length of an uncut portion may progressively vary along the length of the first and/or second segment (or along the length of the catheter or shaft). As an example, the longitudinal spacing of the first or second segment may progressively increase along the length of the first and/or segment, and the ratio may progressively increase along the length of the first and/or second segment.

In yet other embodiments, the slotted portion is configured to provide the flexible and hollow shaft with flexibility to traverse at least two bends having angles of at least or up to 90 degrees during advancement through the patient. In further embodiments, the slotted portion is configured to provide the flexible and hollow shaft with flexibility to traverse at least three bends up having angles of at least or up to 90 degrees during advancement through the patient.

In some embodiments, a ratio of an area of the slotted portion of the flexible and hollow shaft without slotted openings relative to an area of the slotted portion with slotted openings has a value up to 50%. In some embodiments, the ratio may be greater than 50%. The slotted openings may be laser-cut. The flexible and hollow shaft may be formed out of a hypotube. The flexible and hollow shaft may include at least one of a non-slotted portion extending proximally relative the slotted portion or a non-slotted portion extending distally relative the slotted portion. The flexible and hollow shaft may be constructed out of one or more of stainless steel, nitinol, chromium, cobalt, platinum, or polymer. In some embodiments, the flexible and hollow shaft is operably coupled to or in fluid communication with one or more of a catheter control handle, aspiration source, inflation source, or fluid delivery source.

In some embodiments, the flexible and hollow shaft does not include a coil or braided material. The catheter may include an outer liner extending coaxially around the flexible and hollow shaft. In certain embodiments, the flexible and hollow shaft does not include an inner liner extending coaxially within the flexible and hollow shaft. The outer liner may have a uniform hardness along its length.

In accordance with another aspect of the invention, a method for positioning a distal access support catheter within a vasculature of a patient is provided that includes the steps of advancing a distal access support catheter into a patient, the distal access support catheter includes a flexible and hollow shaft including a proximal end and a distal end, the flexible and hollow shaft including a slotted portion with a plurality of slotted openings, wherein the slotted portion includes a first segment with a first pattern of slotted openings and a second segment extending proximally relative the first segment with a second pattern of slotted openings different from the first pattern. The method further includes bending the slotted portion of the flexible and hollow shaft in at least two spaced apart locations while advancing the catheter through the vasculature of the patient.

In some embodiments, the method further includes advancing at least one of a delivery catheter, aspiration catheter, or intravascular device into the patient through or via the flexible and hollow shaft.

In accordance with another aspect of the invention, a method for aspirating an obstruction from a vasculature of a patient is provided that includes advancing an aspiration catheter into a patient distally of an obstruction, the aspiration catheter comprising a flexible and hollow shaft including a proximal end and a distal end, the flexible and hollow shaft including a slotted portion with a plurality of slotted openings, wherein the slotted portion includes a first segment with a first pattern of slotted openings and a second segment extending proximally relative the first segment with a second pattern of slotted openings different from the first pattern. The method further includes bending the slotted portion of the flexible and hollow shaft in at least two spaced apart locations while advancing the catheter through the vasculature of the patient and aspirating the obstruction out of the patient through the flexible and hollow shaft.

In accordance with another aspect of the invention, method for manufacturing a distal access support and/or aspiration catheter is provided that includes cutting a first pattern of slotted openings in a first segment of an elongated, hollow shaft and cutting a second pattern of slotted openings in a second segment of the elongated, hollow shaft, the second segment extending proximally relative the first segment, and the second pattern of slotted openings being different from the first pattern of slotted openings. The method may include coupling an inner liner to an inner surface of the flexible and hollow shaft without an intermediary layer therebetween. The method may further include coupling an outer liner to an outer surface of the flexible and hollow shaft such that the flexible and hollow shaft is sandwiched between the inner and outer liners, the outer liner having a uniform thickness along its length.

BRIEF DESCRIPTION OF THE DRAWINGS

FIG. 1J illustrates an example of one or more segments of the catheter or shaft having a progressively varying pitch and a progressively varying cut pattern.

FIG. 1K illustrates an example embodiment of a catheter or shaft having three distinct segments.

FIGS. 3A-3C illustrate the process of expanding the expandable basket 202 within a vasculature having an obstruction.

FIGS. 5A and 5B are flowcharts illustrating exemplary methods of positioning a distal access support catheter or aspiration catheter, respectively, in accordance with other aspects of the invention.

DETAILED DESCRIPTION OF THE INVENTION

Figure 1A:
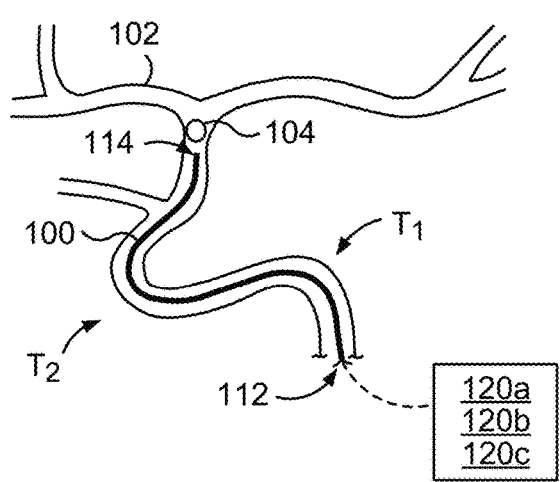
FIGS. 1A and 1B are illustrations of a distal access support and/or aspiration catheter or shaft extending within a vasculature of a patient in accordance with aspects of the invention.
Figure 1B:
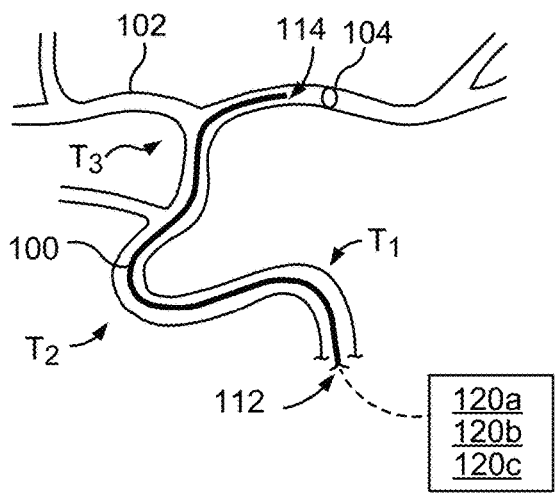

With reference to FIGS. 1A-5C, embodiments of a catheter or shaft 100 for use with various medical devices and procedures are illustrated. In some embodiments, the catheter or shaft 100 may be configured to be used as a distal access support and/or aspiration catheter. For example, the catheter or shaft 100 as described herein may be advanced at least partially into a vasculature 102 (e.g., neurovasculature) of a patient to a desired position (e.g., proximal or distal an obstruction 104). In some embodiments, the catheter may be used as an intermediate support catheter configured to support one or more other catheters slidable therethrough (e.g., a delivery catheter, aspiration catheter, fluid delivery catheter, imaging device catheter). For example, a delivery catheter configured to carry a medical device, such as an intravascular device (e.g., a mechanical thrombectomy device, flow diverter, filter, imaging device, embolization coil, stent, occlusion device) may be slid or otherwise moved through the catheter or shaft 100 in order to position the intravascular device within the patient. In other embodiments, the catheter or shaft 100 may be formed as the actual delivery catheter or delivery shaft coupled to (e.g., directly) or configured to carry the medical device or intravascular device. For example, the catheter or shaft 100 may be configured to be used as the delivery catheter to deliver directly such intravascular devices or imaging devices (e.g., without one or more inner or intermediary catheters extending therethrough). As another example, the catheter or shaft 100 may be a shaft (or hypotube) that is directly coupled to an expandable basket at the distal end of the catheter or shaft 100. In this example, the catheter or shaft 100 may be advanced into a vasculature 102 through a delivery catheter, and may then be extended from the delivery catheter to a desired position. Related intravascular devices and systems, including thrombectomy devices and filters or flow diverters, stents, occlusion devices, aspiration catheters, delivery catheters or shafts applicable to the present invention are described in greater detail below and in co-assigned and previously filed U.S. Provisional Application Nos. 62/677,870, entitled Integrated Thrombectomy and Filter Device and Methods of Use and 62/697,644, entitled Integrated Thrombectomy and Filter Device and Methods of Use; and U.S. patent application Ser. No. 15/842,228, entitled Electrospun Stents, Flow Diverters, and Occlusion Devices and Methods of Making the Same, all of which are incorporated herein by reference for all purposes in their entirety.

Other types of catheters including aspiration catheters or catheters for imaging devices may also be slid or otherwise moved through the catheter or shaft 100. In yet other embodiments, the catheter or shaft 100 may be used directly as an aspiration, imaging, delivery, or fluid delivery catheter as discussed above. For example, the catheter or shaft 100 may be coupled to an aspiration source and used to aspirate the obstruction 104 out of a patient's vasculature. As used herein, the term "obstruction" includes, but is not limited to, a thrombus, embolus, or other particulate. In some embodiments, the catheter or shaft 100 may be configured or sized to be used as one or more of a distal access support catheter, delivery catheter, or aspiration catheter.

While referring in particular to distal access support and/or aspiration catheters for use (e.g., for positioning, supporting, or aspirating) with for example, thrombectomy devices within the neurovasculature (e.g., lumen or vessel within a head, neck, or brain) of a patient, the present invention is not limited to any specific context. For example, such catheters and methods disclosed herein may be used in the coronary or pulmonary vasculature (e.g., to retrieve a pulmonary embolism), the peripheral vasculature (e.g., to retrieve a deep vein thrombus), or in the context of other procedures (e.g., vasospasm, carotid stenting, angioplasty, temporary vessel occlusion, aneurysm bridging). For example, the catheters disclosed herein may be used with a filtering device (e.g., instead of or in addition to a mechanical thrombectomy device) during a thrombectomy procedure or other procedures (e.g., cardiac procedures such as valve replacement, breaking up or dissolution of a thrombus or other obstruction). Other devices or procedures the catheters disclosed herein may be used with or to position include imaging devices, occlusion devices, flow diverters, embolization coils, or stents.

Figure 2:
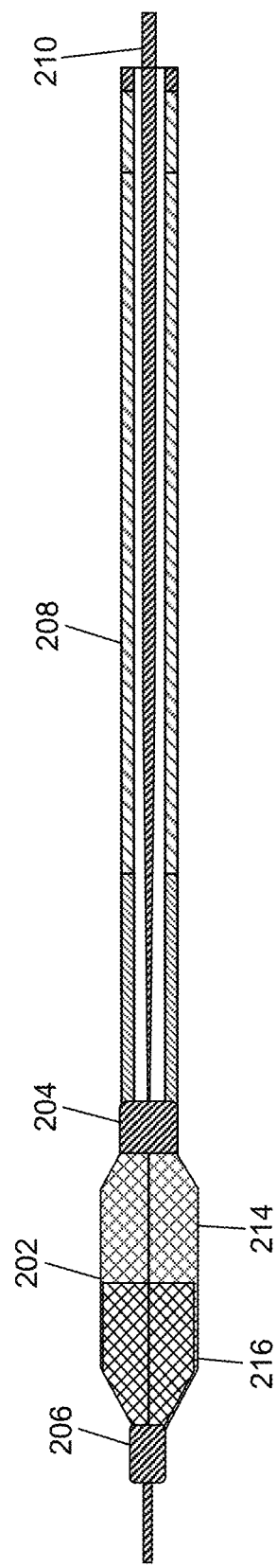
FIG. 2 illustrates an example catheter or shaft that may be a part of an intravascular device.

FIG. 2 illustrates an example catheter or shaft that may be a part of an intravascular device. In some embodiments, the catheter or shaft may be an intravascular-device shaft. For example, the catheter or shaft may be directly coupled to, or part of an intravascular device for engaging, retrieving, capturing, filtering, or removing an obstruction. As used herein, the term "obstruction" includes, but is not limited to, a thrombus, embolus, clot, or other particulate. In these embodiments, the catheter or shaft may comprise a shaft (or hypotube) 208 that is directly coupled to an expandable basket 202 at the distal end of the shaft 208. The intravascular device may additionally, or instead, be configured to provide protection from distal emboli or other obstructions (e.g., as a filtering device) during removal or aspiration of the obstruction or another intravascular procedure (e.g., to remove, dissolve, or break up the obstruction). The expandable basket 202 may be movable between a collapsed configuration and an expanded configuration (and a partially expanded configuration, as illustrated in FIG. 2). The expandable basket 202 is configured to be in the collapsed configuration during delivery or insertion into a vasculature (e.g., a neurovasculature) of the patient and in the expanded configuration during engagement and retrieval or filtering of the obstruction.

The expandable basket 202 may include a proximal end 204 and a distal end 206. The proximal end 204 may be centrally and pivotally coupled to the shaft 208 allowing the expandable basket 202 to pivot and maintain contact with a vessel wall. The distal end 206 may be coupled to an inner wire 210 (e.g., an actuating wire, core wire, delivery wire) extending coaxially through the outer delivery shaft 208. At least one of the proximal end 204 or the distal end 206 may be movable relative to each other such that a proximal portion 214 of the expandable basket 102 is invertible into or towards a distal portion to 216 of the expandable basket 202 to form a proximally oriented cavity in the expanded configuration. The proximally oriented cavity 212 may have a parabolic-shaped cavity formed by the inverted proximal portion 214 of the expandable basket 202.

FIGS. 3A-3C illustrate the process of expanding the expandable basket 202 within a vasculature 102 having an obstruction 104. FIG. 3A illustrates the introduction, via a delivery catheter 209 into the vasculature 102, of an intravascular device that comprises the shaft 208 coupled to the expandable basket 202 (illustrated in FIG. 3A in its constraint configuration). The expandable basket 202 may be advanced to a location distal to the obstruction 104. The delivery catheter 209 may be withdrawn and the expandable basket 102 may be expanded outward to a partially expanded configuration (e.g., due to the lack of constriction provided by the delivery catheter 209) as shown in FIG. 3B. As shown in FIG. 3C, the expandable basket 202 may be inverted into its expanded configuration, thereby forming the proximally oriented cavity 212, which may be used to engage, retrieve, capture, filter, or remove an obstruction.

Figure 4:
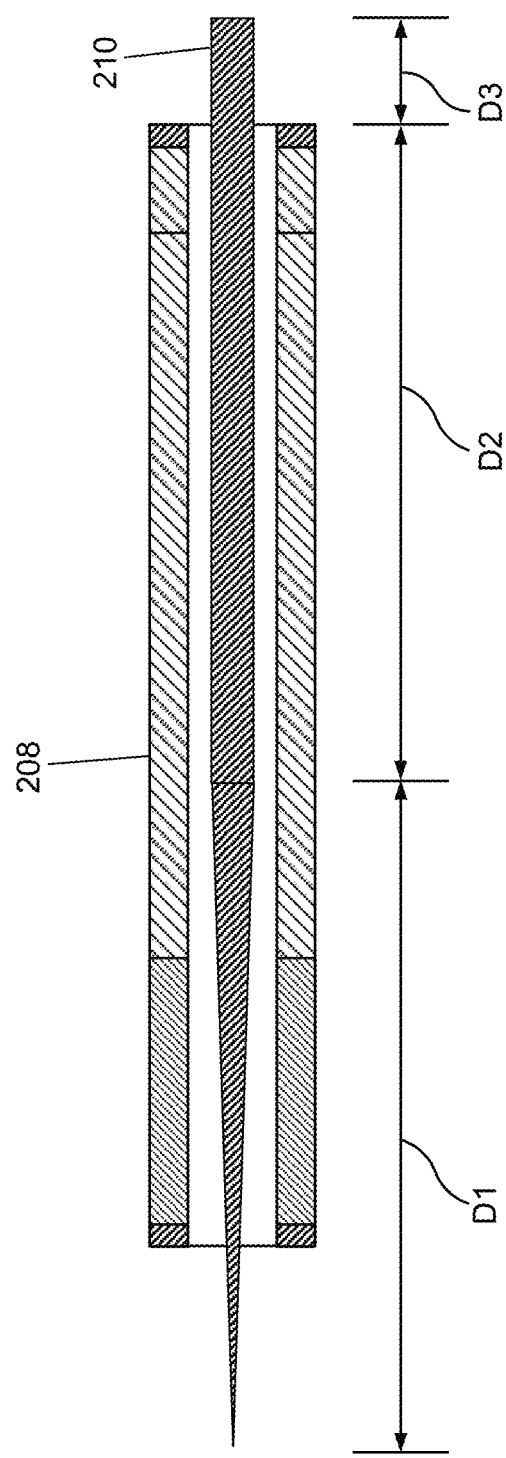
FIG. 4 illustrates a close-up view of the inner wire within the shaft.

FIG. 4 illustrates a close-up view of the inner wire 210 within the shaft 208. FIG. 4 omits the expandable basket 202. In some embodiments, as illustrated in FIG. 2 and FIG. 4, the inner wire 210 may have a smaller diameter at a distal end or portion relative to a proximal end or portion. For example, the inner wire 210 may taper down in diameter from near or proximate to where the shaft 208 is coupled to the proximal end 204 of the expandable basket 202 to the distal end 206 of the expandable basket 202. Decreasing or tapering the diameter of the inner wire 210 enhances flexibility for bending or pivoting of the inner wire 210 at the distal portion of the inner wire 210 while providing sufficient stiffness at the proximal portion of the inner wire 210. FIG. 4 illustrates this tapering portion as segment D1. Segment D1 may be of any suitable size. As an example, segment D1 may be about 40 cm. In some embodiments, a more proximal segment of the inner wire 210, may not have a taper (e.g., it may be cylindrical), illustrated in FIG. 4 as segment D2. Segment D2 may be of any suitable size. As an example, segment D2 may be about 140 cm to 145 cm. In some embodiments, a segment of the inner wire 210, may extend beyond the proximal end of the shaft 208, illustrated in FIG. 4 as segment D3. Segment D3 may be of any suitable size. As an example, segment D3 may be about 0.007" to 0.0118" in length. The proximal portion of the inner wire 210 requires sufficient stiffness to allow application of a push-pull force upon the inner wire 210 to expand the basket 202 or for retrieval of the basket 202. Tapering from a larger diameter to a smaller diameter along a length of the inner wire 210 allows the inner wire 210 to have a larger diameter along a proximal end or portion of the inner wire 210 relative to the distal end or portion. Additionally, a smaller diameter at a distal end or portion of the inner wire 210 may provide increased clearance between an outer diameter of the inner wire 210 and an inner diameter of the outer delivery shaft 208 to reduce friction between the components during actuation of the expandable basket 202. Further, the inner wire 210 may have a coating (e.g., a PTFE coating) to allow it to slide or move more easily (e.g., reduce friction) relative to the outer delivery shaft 208. In some embodiments, the inner wire 210 may be flattened at or near the distal end of the inner wire 210 (for example, the portion of the inner wire distal to the expandable basket 202). In some embodiments, the inner wire 210 may be cylindrical until the flattened portion—i.e., it may have a cylindrical portion and a flattened portion. By flattening the inner wire 210, the distal end of the inner wire one may be made more flexible and easy to deflect, and may consequently facilitate navigation through pathways that may have tight turns requiring increased maneuverability. More information about intravascular devices for engaging, retrieving, capturing, filtering, or removing an obstruction may be found in U.S. patent application Ser. No. 16/425,650, entitled Integrated Thrombectomy and Filter Device and Methods of Use, which is incorporated by reference herein in its entirety for all purposes.

With reference to FIGS. 1A-1I, the catheter or shaft 100 as described herein includes an elongate, flexible and hollow shaft 110 (e.g., cannula, tube, sheath) including a proximal end 112 and a distal end 114. The shaft 110 includes a slotted portion 116 with a plurality of slotted openings 118 (e.g., cuts, slits, apertures, grooves). The slotted openings 118 provide the slotted portion 116 with varying flexibility or stiffness along a length of the slotted portion 116. For example, the shaft 110 may bend or flex to traverse two or more turns, curves, or bends (e.g., T1 and T2) having angles of at least or up to 90 degrees (see FIG. 1A) as the catheter or shaft 100 is advanced into a desired position within a patient through the vasculature 102. In other embodiments, the shaft 110 may have a sufficient flexible distal length to bend or flex to traverse three or more turns, curves, or bends (e.g., T1-T3) having angles of at least or up to 90 degrees (see FIG. 1B) as the catheter or shaft 100 is advanced into a desired distal position within a patient through the vasculature 102. In such embodiments, the desired position may be more distal (e.g., longer path to traverse) within a patient's body and includes more turns such that the flexible portion (e.g., distal portion) of the catheter or shaft 100 is greater in length relative to the flexible portion in FIG. 1A.

The shaft 110 may possess sufficient structural integrity to traverse the turns without ovalizing or kinking. For example, in some embodiments, a ratio or proportion of non-slotted area to slotted area along any length of the shaft 110 (e.g., measured circumferentially) may be about, greater than or equal to 50% to provide the structural integrity or rigidity. In some embodiments, the ratio or proportion of non-slotted area to slotted area of the shaft 110 includes or is between 40% to 50%, 50% to 70%, 50% to 80%, or any value therebetween.

In some embodiments, a distal portion of the slotted portion 116 may be provided with more densely packed slotted openings (e.g., more openings, larger opening, or openings spaced closer together) relative to a proximal portion as described in more detail below. This may provide the distal portion with increased flexibility relative to the proximal portion while maintaining sufficient structural integrity or rigidity at the proximal portion in order to advance the shaft 110 into position within the patient (e.g., by applying push-pull forces on the stiffer or less flexible proximal portion). For example, in some embodiments, the distal portion or end of the catheter or shaft 100 may bend or turn greater than 90 degrees in any direction (e.g., without ovalizing or kinking). Further, in some embodiments, wall thickness or outer diameter of the shaft 110 may be reduced or inner diameter increased relative to conventional (e.g., braided or coiled) catheters as described in more detail below. Therefore, space is increased between an inner diameter or wall of the catheter or shaft 100 and intravascular devices or catheters positioned or supported therein or extending therethrough for delivery. Such increased space may provide room for contrast to be injected between the inner wall of the catheter or shaft 100 and the devices or catheters for aiding a clinician in positioning the devices or catheters. Additionally, decreasing the wall thickness or outer diameter or increasing the inner diameter may reduce an overall profile of the catheter or shaft 100 for improved positioning in or through narrow spaces (e.g., within a patient vasculature).

The slotted openings 118 may be formed by a laser-cutting process or other suitable process (e.g., etching) for removing material from the shaft 110. For example, the catheter or shaft 100 may be a laser-cut hypotube. The slotted openings 118 may extend partially or completely through walls of shaft 110. The slotted openings 118 may be formed or extend at an angle (e.g., obliquely or orthogonally) relative to a longitudinal axis of the shaft 110. For example, the slotted openings 118 may extend in a helical or spiral pattern about the shaft 110. In some embodiments, a helical or spiral pattern (e.g., extending obliquely relative the longitudinal axis) may be easier to manufacture or cut relative to slotted openings extending in a non-helical manner at an orthogonal angle. The catheter or shaft 100 may be formed or constructed out of one or more of stainless steel, nitinol, platinum, chromium, cobalt, nickel, other suitable metallic material, polymer, or other suitable material. For example, the shaft 110 may be constructed of multiple layers (e.g., an inner platinum layer and an outer cobalt nickel layer). Further, the catheter or shaft 100 may include radiopaque material or marker bands (e.g., coupled to an inner distal end) for indicating location to a clinician during or to verify placement within the patient. In some embodiments, the catheter or shaft 100 is gold-plated.

Figure 1C:
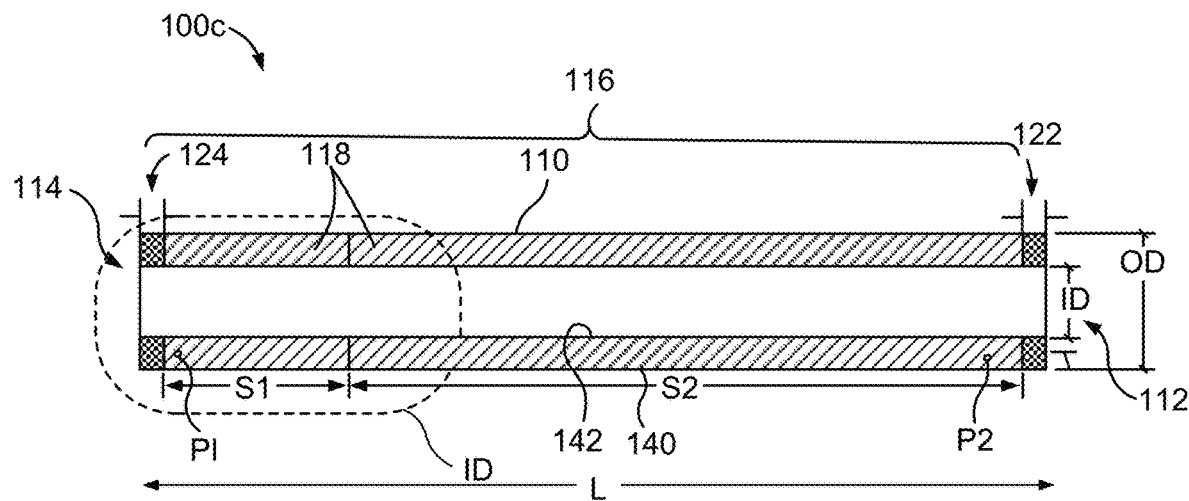
FIGS. 1C and 1D are side section and detailed views, respectively, of the catheter or shaft of FIG. 1A or FIG. 1B configured in accordance with an aspect of the invention.
Figure 1D:
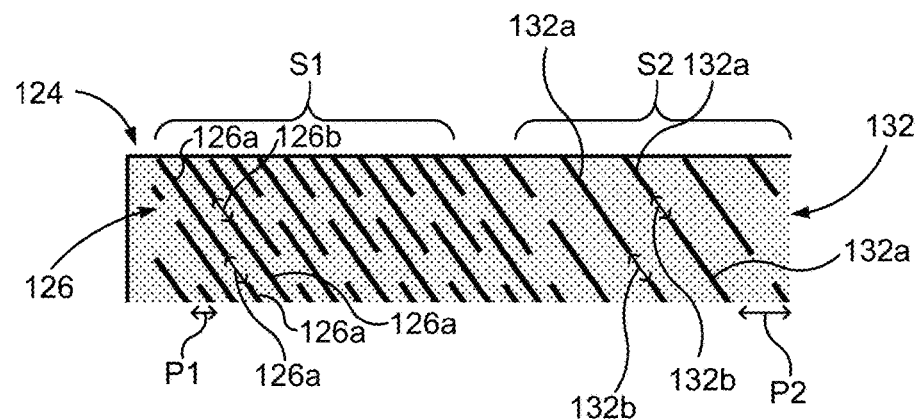

FIGS. 1C-1D are side section and detailed views, respectively, of a catheter or shaft 100*c* configured in accordance with an embodiment of the present disclosure. The catheter or shaft 100*c* may be configured to be a distal access support catheter (e.g., for supporting other catheters, including delivery catheters, intravascular devices, or both) and/or aspiration catheter as described herein. The slotted portion 116 includes a first segment S1 with a first pattern of slotted openings 126 and a second segment S2 extending proximally (e.g., disposed proximal) relative the first segment S1 with a second pattern of slotted openings 132 different from the first pattern 126. The slotted openings 118 are discontinuous (e.g., do not extend circumferentially around the shaft 110 in a continuous manner or 360 degrees). In other words, the slotted openings 118 include cut and uncut portions (e.g., slotted and un-slotted, removed and solid, or grooved and un-grooved portions) as described in more detail below.

While illustrated with two slotted segments, S1 and S2, in some embodiments, the slotted portion 116 may include more than two slotted segments. For example, the slotted portion 116 may include three, four, five, or more slotted segments. Each of the segments may have different patterns relative to the other segments. In other embodiments, two or more of the segments may have similar or the same pattern. In some embodiments, each of the segments may have one or more patterns (e.g., different patterns) of slotted openings. For example, segment S1 may have a first pattern of slotted openings (e.g., along a distal portion) and a second pattern of slotted opening (e.g., along a proximal portion) different from the first pattern (See FIG. 1I). The segment S2 may then have a third pattern of slotted openings and/or fourth pattern of slotted openings different from the pattern(s) of the first segment S1. In some embodiments, at least one of the pattern(s) of the segment S2 may the same as at least one of the pattern(s) of segment S1.

The first pattern of slotted openings 126 may include a repeating helical pattern of cut and uncut portions 126*a* and 126*b* extending circumferentially around and along a length of the first segment S1. Similarly, the second pattern of slotted openings 132 may include a repeating helical pattern of cut and uncut portions 132*a* and 132*b* extending circumferentially around and along a length of the second segment S2. The cut and uncut portions of each pattern may extend at equivalent angles (e.g., oblique or orthogonal) relative to the longitudinal axis of the shaft 110. As described above, in some embodiments, a longitudinal spacing between the slotted openings 118 may be closer or smaller at a distal portion (e.g., along segment S1) of the shaft relative to a proximal portion (e.g., along segment S2) such that the openings are more densely packed along the distal portion (e.g., more material removed in that portion) resulting in greater flexibility along the distal portion relative the proximal portion. In this manner, the distal portion (e.g., S1) is provided with sufficient flexibility to traverse turns or bends within a patient's vasculature and sufficient length to reach a desired location within the patient. For example, a length of such a distal portion may be increased proportionally relative to how distal a location the catheter is to be positioned within the patient. Additionally, the proximal portion (e.g., S2) is provided with sufficient rigidity such that push-pull forces applied to the proximal end may be transferred to advance the catheter therethrough.

In some embodiments, the proximal end 112 includes a solid or uncut portion 122 (e.g., un-slotted) extending proximally relative to segment S2 and the distal end 114 includes a solid or uncut portion 124 (e.g., un-slotted) extending distally relative to segment S1. The proximal solid portion 122 may have a length with values of or between 0.01" to 0.02", 0.012" to 0.018", 0.014" to 0.016", or any value therebetween (e.g., 0.014"). The distal solid portion 124 may have a length with values of or between 0.001" to 0.006", 0.002" to 0.005", 0.003" to 0.004", or any value therebetween (e.g., 0.0031").

In some embodiments, a pitch or spacing between cut portions may vary or increase from pitch P1 at a distal end to pitch P2 at the proximal end of the slotted portion. Further, in some embodiments, a longitudinal spacing or pitch P1 between cut portions 126a of the first pattern 126 may be smaller relative to the longitudinal spacing or pitch P2 (e.g., P1<P2) between cut portions 132a of the second pattern 132 such that a density or number of slotted openings in the first segment S1 is greater than a density or number of slotted openings in the second segment S2 (e.g., providing greater relative flexibility). Similarly, the longitudinal spacing or pitch between uncut portions 126b of the first pattern 126 may be smaller relative to the longitudinal spacing or pitch between uncut portions 132b of the second pattern 132. In some embodiments, the pitch or spacing may be constant along a segment or segments.

Figures 1E, 1F, 1G:
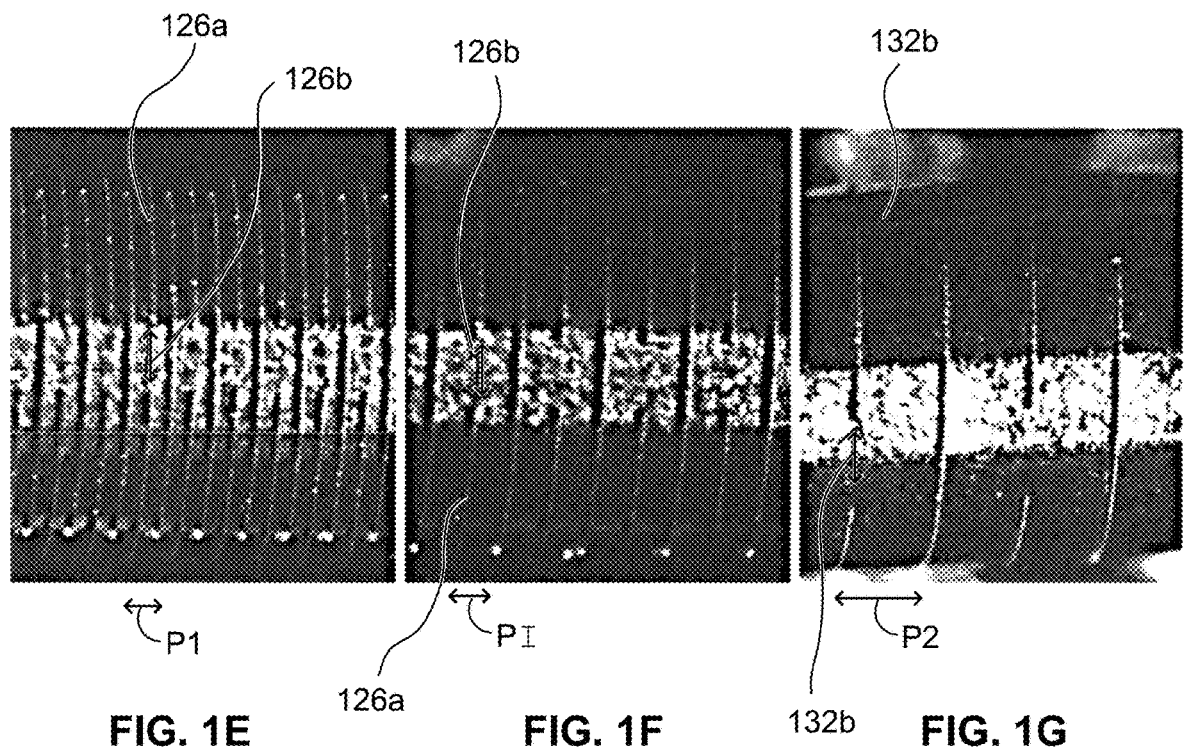
FIGS. 1E-1G are detailed views of the catheter or shaft of FIG. 1C taken along different locations along a length of the catheter or shaft having a progressively increasing pitch from the distal end to the proximal end in accordance with aspects of the invention.

In other embodiments, the longitudinal spacing or pitch along a length of the shaft 110 gradually or progressively increases from the distal end 114 to the proximal end 112 (e.g., from distal end of the first pattern 126 to a proximal end of the second pattern 132) such that it varies across each segment. For example, pitch may progressively increase along the length of one or more segments rather than being constant across segments such that the pitch or longitudinal spacing transitions from pitch P1 to pitch P2 along the length of the shaft. In this manner, the pitch or longitudinal spacing between cut portions between the distal and proximal ends may have a value greater than P1 but less than P2. For example, as illustrated in detailed views (FIGS. 1E-1G) of three spaced apart longitudinally spaced apart locations of the shaft 110, the pitch or longitudinal spacing may vary or progressively increase along a length of the slotted portion of the shaft from pitch P1 at a distal portion (FIG. 1E), to pitch PI at an intermediary portion between distal and proximal portions (FIG. 1F), and to pitch P2 at a proximal portion (FIG. 1G). In some embodiments, the distal, intermediary, and proximal portions may correspond to locations about 1", 6", and 47", respectively, from a distal end of a shaft having an overall length of about 50" (e.g., with segment S1 of about 10" and S2 about 40". In some embodiments, these locations may correspond to locations proximate or near a distal end of segment S1, proximal end of segment S1, and proximal end of segment S2, respectively. For example, referencing FIG. 1H, the pitch or longitudinal spacing may transition from a first pitch P1 to a second pitch P2 along the length of the segment S1, and then to a pitch P3 at segment S2 (e.g., a proximal end of segment S2). In these embodiments, pitch may progressively increase along the length of an individual segment rather than being constant across the entirety of the segment. In some embodiments, the pitch P1 may have a value of or between 0.001" to 0.006", 0.002" to 0.005", 0.003" to 0.004", or any value therebetween (e.g., 0.0031"). In some embodiments, the pitch P2 may have a value of or between 0.01" to 0.02", 0.012" to 0.018", 0.014" to 0.016", or any value there between (e.g., 0.015").

As discussed above, the repeating helical patterns of the first pattern or second pattern include cut and uncut portions. Each cut portion is spaced circumferentially from another cut portion by an uncut portion such that the repeating helical pattern includes alternating cut and uncut portions extending circumferentially around the shaft of each slotted segment. In some embodiments, an arc length of cut portions has a value of or between 80 degrees to 150 degrees or any value therebetween (e.g., 124, 116 degrees, 104 degrees). In some embodiments, an arc length of uncut portions has a value of or between 10 degrees to 60 degrees or any value therebetween (e.g., 20 degrees, 28 degrees, 40 degrees). In some embodiments, a combined arc length of adjacent cut and uncut portions of the helical pattern of the first pattern or second pattern of slotted openings has a value of or between 100 degrees and 180 degrees, 120 degrees to 160 degrees, 130 degrees to 150 degrees, 135 degrees to 145 degrees, or any value therebetween (e.g., 144 degrees).

As used herein, the term "cuts per revolution" or "CPR" refers to the number of combined adjacent cut and uncut portions required to completely extend around the shaft 110 (e.g., in one revolution or 360 degrees) determined based on the combined arc length of the adjacent cut and uncut portions. For example, when adjacent cut and uncut portions of the first pattern or second pattern of slotted openings 126 or 132 have a combined arc length of 144 degrees (e.g., 124 degrees cut portion arc length and 20 degrees uncut portion arc length or 116 degrees cut portion arc length and 28 degrees uncut portion arc length), the CPR is 2.5. That is, the product of 2.5 and the combined arc length is equivalent to a single, complete revolution around the shaft (e.g., 360 degrees). In some embodiments, segments S1 and S2 (e.g., first pattern and second pattern of slotted openings 126 and 132) may have equivalent CPR's. However, in other embodiments, they may be different. In some embodiments, the CPR of a segment may have a value of or between 1-8, 2-7, 3-6, 4-5, 2-3, 2-4, or any value therebetween.

Additionally, in some embodiments, while CPR or combined arc length of cut and uncut portions may be constant across each segment or segments, one or more of pitch, width, arc length of cut portions, or arc length of uncut portions may be different or varied across each segment or segments. For example, the first and second segments S1 and S2 may each have CPR's of 2.5 or a combined arc length of cut and uncut portions of 144 degrees. However, the first segment S1 may have cut portions with arc lengths of 124 degrees and uncut portions with arc lengths of 20 degrees while the segment S2 may have cut portions with arc lengths of 116 degrees and uncut portions with arc lengths of 28 degrees. Increasing arc length of cut portions in segment S1 relative to arc length of cut portions in segment S2 may increase flexibility (e.g., varying flexibility along the length) in the segment instead of or in addition to decreasing pitch or longitudinal spacing (e.g., increasing density of slotted opening). In this manner, segment S1 is also more flexible as the arc length of its cut portions are relatively greater than the arc length of the cut portions of the segment S2. In other embodiments, one or more of CPR or combined arc length of cut and uncut portions, pitch, width, arc length of cut portions, or arc length of uncut portions may be varied or constant across each segment or segments. Further, the varying arc length and spacing as described herein may also provide the catheter or shaft 100 with sufficient flexibility or structural integrity (e.g., to prevent or reduce ovalizing or kinking) while improving dimensional characteristics of the catheter or shaft 100c (e.g., reduced outer diameter or wall thickness or increased inner diameter) relative to conventional catheters as described in more detail below.

As an alternative to CPR, segments of the catheter or shaft 100 may be characterized by one or more respective cut patterns. As used herein, the term "cut pattern" refers to the ratio of the cut portion arc length to the uncut portion arc length. For example, a cut pattern of 124/20 indicates a cut portion arc length of 124 degrees and an uncut portion arc length of 20 degrees. This may be expressed with less specificity as having a CPR of 2.5, as discussed above. As with pitch, the cut pattern may vary gradually or progressively along the length of the catheter or shaft 100. In some embodiments, the cut pattern may progressively decrease from the distal end 114 to the proximal end 112. In some embodiments, as with pitch, the cut pattern may progressively decrease within an individual segment. Increasing the cut pattern increases flexibility. For example, a cut pattern of 124/20 provides for a relatively flexible segment of the catheter shaft 100, while a cut pattern of 79/65 provides for a relatively rigid segment.

In some embodiments, both the cut pattern and the pitch may vary gradually or progressively across the length of the catheter or shaft 100. As discussed above, the cut pattern and/or pitch may be varied to affect the local flexibility (or rigidity) of a segment of the catheter or shaft 100. Abrupt transitions in flexibility may have the undesired effect of compromising the integrity of the catheter or shaft 100, or of increasing the risk of kinking (e.g., at the juncture between two segments of different flexibility). Varying the transition gradually or progressively serves to prevent or reduce these undesired effects. In some embodiments, varying both cut pattern and pitch may allow for a smoother transition between segments. For example, to achieve a desired flex ability, the cut pattern and the pitch may each be varied by a relatively small amount. To achieve the same flexibility while varying only one of either the cut pattern or pitch, a relatively large amount may need to be varied. Essentially, the ability to vary both the cut pattern and the pitch may provide more degrees of freedom in changing local flexibility. In some embodiments, achieving certain levels of flexibility without compromising the integrity of the catheter or shaft 100 may require varying both cut pattern and pitch. For example, increasing the cut pattern beyond a threshold ratio may significantly reduce the integrity of a segment (e.g., because increasing the cut pattern inherently involves cutting and removing material from the segment). The same may hold true for decreasing the pitch beneath a threshold pitch. FIG. 1J illustrates an example of one or more segments of the catheter or shaft 100 having a progressively varying pitch and a progressively varying cut pattern. As an example, referencing FIG. 1J, the segment S1 may have a pitch that progressively varies from P1 to P2 (e.g., 0.0025" to 0.010") and a cut pattern that progressively varies from C1 to C2 (e.g., 124/20 to 99/45). In this example, the segment S2 may have a constant pitch P2 (e.g., 0.010") and a constant cut pattern C2 (e.g., 99/45). Also in this example, the segment S3 may have a constant pitch of P2 (e.g., 0.010") and a cut pattern that progressively varies from C2 to C3 (e.g., 99/45 to 79/65).

FIG. 1K illustrates an example embodiment of a catheter or shaft having three distinct segments. Each of these segments—S1, S2, and S3—may have different pitch, cut pattern, CPR, and lengths, as outlined in the table below, listing different embodiments ("items"). For example, item 1 is an embodiment that has a segment S1 that has a length of 30 cm, a varying pitch that varies (e.g., progressively) from 0.0027" to 0.010", a cut pattern that that varies (e.g., progressively) from 124/20 to 104/40, and a CPR of 2.5. In this example, item 1 also has a segment S2 that has a length of 135 cm and a segment S3 that has a length of 0.025 cm (or 0.010"). In this example, segments S2 and S3 are not slotted.

| | | S1 | | | | S2 | | | | S3 | | |
|---|---|---|---|---|---|---|---|---|---|---|---|---|
| Item | Length | Pitch | Cut Pattern | CPR | Length | Pitch | Cut Pattern | CPR | Length | Pitch | Cut Pattern | CPR |
| 1 | 30 cm | 0.0027" → 0.010" | 124/20 → 104/40 | 2.5 | 135 cm | N/A | N/A | N/A | .010" (.025 cm) | N/A | N/A | N/A |
| 2 | 30 cm | 0.0027" → 0.010" | 124/20 → 104/40 | 2.5 | 135 cm | .010" | 104/40 | 2.5 | .010" (.025 cm) | N/A | N/A | N/A |
| 3 | 40 cm | 0.0025" → 0.010" | 124/20 → 99/45 | 2.5 | 118 cm | 0.010" | 99/45 | 2.5 | 10 cm | 0.010" | 99/45 → 79/65 | 2.5 |
| 4 | 40 cm | 0.0025" → 0.010" | 124/20 → 99/45 | 2.5 | 118 cm | 0.010" | 99/45 | 2.5 | 9 cm | 0.010" | 99/45 → 79/65 | 2.5 |
| 5 | 40 cm | 0.0025" → 0.010" | 124/20 → 99/45 | 2.5 | 133 cm | 0.010" | 99/45 | 2.5 | 9 cm | 0.010" | 99/45 → 79/65 | 2.5 |

In some embodiments, the catheter or shaft 100c has an outer diameter OD having a value of or between about 0.02" to 0.12", 0.04" to 0.09" or any value therebetween (e.g., 0.06", 0.065", 0.07"). The OD may be constant or uniform in some embodiments across the length. The catheter or shaft 100c may have an inner diameter ID having a value of or between 0.02" to 0.08" or any value therebetween (e.g., 0.06", 0.061", 0.062", 0.072"). The ID may be constant or uniform in some embodiments across the length. A wall thickness T of catheter or shaft 100c may have a value of or between 0.001" to 0.005", less than 0.003", or any value therebetween (e.g., 0.0015", 0.002", 0.003", 0.0035", 0.004"). The catheter or shaft 100c may have an overall length L of or between 30 to 80 inches, or any value therebetween (e.g., 45", 50", 55"). Segment S1 may have a length L of or between 5 to 20 inches, or any value therebetween (e.g., 5", 10"). Segment S2 may have a length L of or between 25 to 75 inches, or any value therebetween (e.g., 40", 45", 50").

In some embodiments, the proximal end 112 of the catheter or shaft 100c may be operably coupled to a catheter control handle 120a, fluid source 120b, aspiration source 120c, or energy delivery source. In yet further embodiments, the shaft 110 may include outer or inner layers or jackets 140, 142 (e.g., Teflon, polyurethane, polyether, elastomer, PTFE, polymer or other suitable material liners, layers, coatings) sandwiching the shaft therebetween (e.g., to reduce friction against a patient's vasculature or catheters or other devices supported therein). In some embodiments, the outer or inner layers or jackets 140, 142 may include a hydrophilic or anti-thrombogenic coating. In yet other embodiments, the catheter or shaft 100c does not include an inner jacket 142. For example, an inner liner or coating may not be provided when the catheter is used directly as a delivery shaft for a mechanical thrombectomy device, as an aspiration catheter to increase inner diameter, or when other catheters or devices are not configured to move therethrough. One or more of the outer or inner layers or jackets 140, 142 may be directly applied, adhered, coated, or otherwise coupled to the shaft 110 (e.g., without intermediary, strike, or adhesive layers therebetween). The inner or outer layer or jacket (e.g., liner) may have a width or thickness of or between 0.00025" to 0.002", or any value therebetween (e.g., 0.001"). Further, in some embodiments, as the shaft's variable flexibility or stiffness is provided by the slotted openings (e.g., without coils or braids for rigidity or support), the shaft 110 may be provided with an outer jacket 140 having a uniform hardness across its length (e.g., reducing overall profile).

Figure 1H:
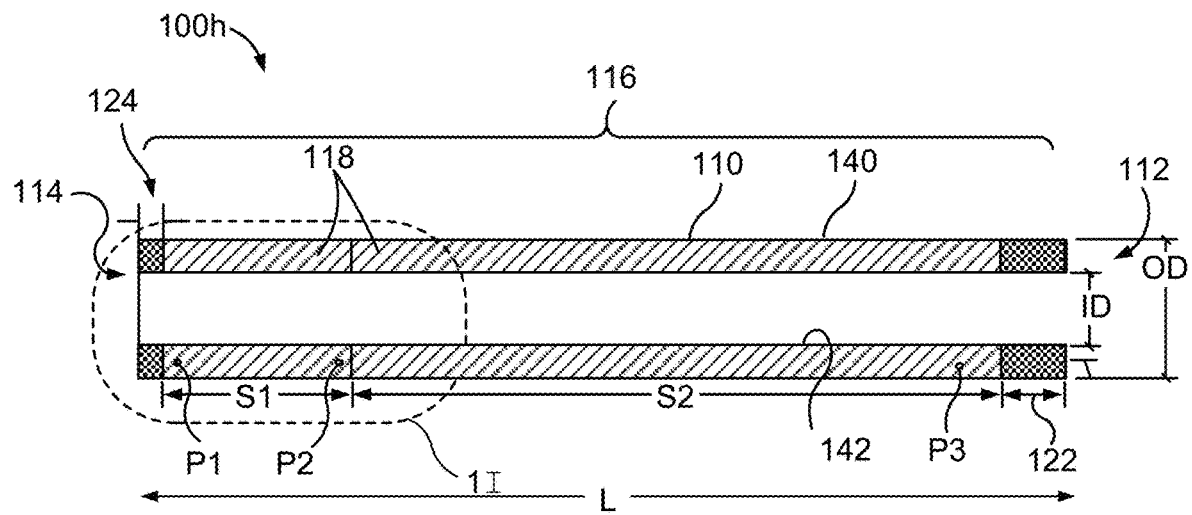
FIGS. 1H and 1I are side section and detailed views, respectively, of the catheter or shaft of FIG. 1A or FIG. 1B configured in accordance with another aspect of the invention.
Figure 1I:
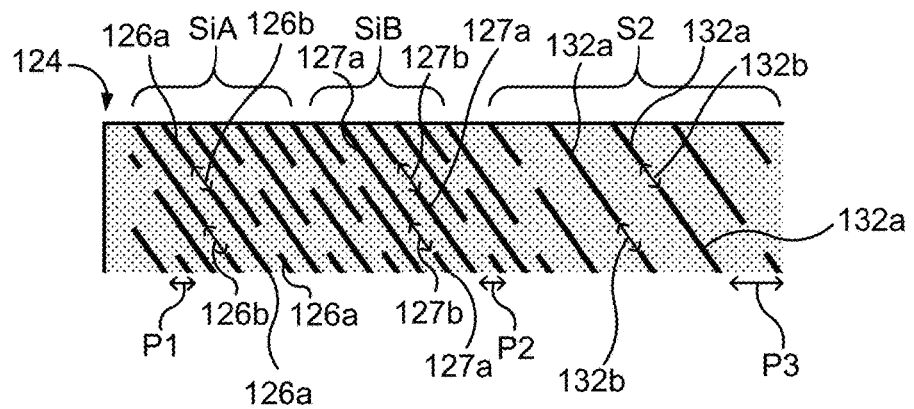

With reference to FIGS. 1H-1I, side section and detailed views, respectively, of a catheter or shaft 100h are illustrated configured in accordance with another embodiment of the present disclosure. The catheter or shaft 100h may be configured to be a delivery catheter or shaft (e.g., coupled to the intravascular device) for directly supporting or positioning an intravascular device such as a thrombectomy or filter device as described in U.S. Provisional Application Nos. 62/677,870 and 62/697,644 incorporated by reference above) as described herein. The catheter or shaft 100h may include one or more of any of the features, in whole or in part, as described above with respect to catheter or shaft 100c. For example, the catheter or shaft 100h includes a slotted portion 116. The slotted portion 116 includes a first segment 51 with a first pattern of slotted openings 126 (e.g., along a distal portion S1A) and a second pattern of slotted openings 127 different from the first pattern (e.g., reduced arc length of cut portions relative to the first pattern along a proximal portion S2A). The slotted portion further includes a second segment S2 extending proximally (e.g., disposed proximal) relative the first segment S1 with a third pattern of slotted openings 132 different from the first pattern 126 (e.g., either the same as the second pattern 127 or reduced arc length of cut portions relatively to the second pattern). However, in some embodiments, segment S2 is solid or uncut and does not include a pattern of slotted openings 118. In yet other embodiments, the segment S1 or other segments only include one pattern (e.g., the first pattern of slotted openings 126). The slotted openings 118 are discontinuous (e.g., do not extend circumferentially around the shaft 110 in a continuous manner or 360 degrees). In some embodiments, the proximal end 112 of the catheter or shaft 100h may be operably coupled to a catheter control handle 120a, fluid source 120b, aspiration source 120c, or energy delivery source.

In some embodiments, the proximal end 112 includes a solid or uncut portion 122 (e.g., un-slotted) extending proximally relative to segment S2 and the distal end 114 includes a solid or uncut portion 124 (e.g., un-slotted) extending distally relative to segment S1. The proximal solid portion 122 may have a length with values of or between 0.005" to 0.03", 0.01" to 0.02", or any value there between (e.g., 0.01"). The distal solid portion 124 may have a length with values of or between 0.001" to 0.006", 0.002" to 0.005", 0.003" to 0.004", or any value therebetween (e.g., 0.0027").

As described above, longitudinal spacing or pitch may increase from a distal end to a proximal end of the slotted shaft. For example, the longitudinal spacing or pitch P1 between cut portions 126a of the first pattern 126 may be smaller relative to the longitudinal spacing or pitch P2 (e.g., P1<P2) between cut portion 127a of the second pattern of segment S1 as well as longitudinal spacing or pitch P3 between cut portions 132a of the third pattern 132 such that a density or number of slotted openings in a distal portion of first segment S1 is greater than a density or number of slotted openings in the proximal portion of first segment S1 or the second segment S2 (e.g., to provide flexibility for traversing bends while maintaining sufficient stiffness along a proximal portion for application or transferring of push-pull forces). In some embodiments P2 is less than P3. In other embodiments P2 is equivalent or equals P3. Similarly, the longitudinal spacing or pitch between uncut portions 126b of the first pattern 126 may be smaller relative to the longitudinal spacing or pitch between uncut portions 127b or 132b. In some embodiments, the pitch P1 has a value of or between 0.001" to 0.006", 0.002" to 0.005", 0.003" to 0.004", or any value therebetween (e.g., 0.0027"). In some embodiments, the pitches P2 or P3 has a value of or between 0.005" to 0.03", 0.01" to 0.02", or any value therebetween (e.g., 0.01").

As discussed above with respect to catheter or shaft 100c, similarly, in some embodiments, the longitudinal spacing or pitch along a length of the shaft 110 of catheter or shaft 100h may gradually or progressively increase from the distal end 114 to the proximal end 112 (e.g., from distal end of the first pattern 126 to the second pattern 127 and then to the proximal end of the third pattern 132. For example, pitch or spacing may progressively increase along the length of one or more segments rather than being constant across segments such that the pitch or longitudinal spacing transitions from pitch P1 to pitch P2 to pitch P3 along the length of the shaft. However, in other embodiments, one or more segments may have constant pitches or longitudinal spacing.

As discussed above with respect to catheter or shaft 100c, the repeating helical patterns of the first pattern, second pattern, or third pattern include cut and uncut portions. In some embodiments, an arc length of cut portions has a value of or between 80 degrees to 150 degrees or any value therebetween (e.g., 124, 116 degrees, 104 degrees). In some embodiments, an arc length of uncut portions has a value of or between 10 degrees to 60 degrees or any value therebetween (e.g., 20 degrees, 28 degrees, 40 degrees). In some embodiments, a combined arc length of adjacent cut and uncut portions of the helical pattern of the first pattern or second pattern of slotted openings has a value of or between 100 degrees and 180 degrees, 120 degrees to 160 degrees, 130 degrees to 150 degrees, 135 degrees to 145 degrees, or any value therebetween (e.g., 144 degrees). In some embodiments, segments S1 and S2 (e.g., first pattern, second pattern, and third pattern of slotted openings 126, 127 and 132) may have equivalent CPR's. However, in other embodiments, one or more of the patterns may have different CPR's.

Additionally, in some embodiments, while CPR or combined arc length of cut and uncut portions may be constant across each segment or segments, pitch, length, arc lengths of cut portions, or arc lengths of uncut portions may be different or varied across each segment or segments. For example, the first and second segments may each have CPR's of 2.5 or a combined arc length of cut and uncut portions of 144 degrees. However, the first segment S1 may have cut portions with arc lengths of 124 degrees and uncut portions with arc lengths of 20 degrees while the segment S2 may have cut portions with arc lengths of 104 degrees and uncut portions with arc lengths of 40 degrees. Further, as described above, a segment (e.g., first segment S1) may have cut portions with arc lengths of 124 degrees and uncut portions with arc lengths of 20 degrees along a distal portion and cut portion with arc lengths of 104 degrees and uncut portions with arc lengths of 40 degrees along a proximal portion. In other embodiments, one or more of CPR or combined arc length of cut and uncut portions, pitch, width, arc length of cut portions, or arc length of uncut portions may be varied or constant across each segment or segments.

In some embodiments, the catheter or shaft 100h has an outer diameter OD having a value of or between about 0.02" to 0.12", 0.01" to 0.03" or any value therebetween (e.g., 0.016", 0.018", 0.02"). The catheter or shaft 100h may have an inner diameter ID having a value of or between 0.01" to 0.03" or any value therebetween (e.g., 0.012", 0.014", 0.016"). A wall thickness T of catheter or shaft 100h may have a value of or between 0.001" to 0.005", less than 0.003", or any value therebetween (e.g., 0.0015", 0.002", 0.003", 0.0035", 0.004"). The catheter or shaft 100h may have an overall length L of or between 40 to 80 inches, or any value therebetween (e.g., 60", 65", 70"). Segment S1 may have a length L of or between 5 to 20 inches, or any value therebetween (e.g., 9", 11". 13"). Segment S2 may have a length L of or between 35 to 75 inches, or any value therebetween (e.g., 50", 55", 60"). In some embodiments, one or more of OD, ID, or T may be uniform across the length. Further, in some embodiments, the catheter or shaft 100h may have inner and outer layer or jackets 140, 142 as described above (e.g., with uniform hardness or directly coupled), be formed without an inner layer or jacket 142, and/or without a coil or braid.

FIGS. 5A-5B illustrate exemplary methods 500a and 500b for positioning a distal access support catheter within a vasculature of a patient and aspirating an obstruction from a vasculature of a patient, respectively. One or more of any steps of methods described herein may be removed, re-ordered, substituted, added, or modified. The method 500a includes the steps of advancing a distal access support catheter into a patient 502a (e.g., via a guidewire or within an outer catheter or sheath). The distal access support catheter includes a flexible and hollow shaft including a proximal end and a distal end as described herein. The shaft includes a slotted portion with a plurality of slotted openings and the slotted portion includes a first segment with a first pattern of slotted openings and a second segment extending proximally relative the first segment with a second pattern of slotted openings different from the first pattern. The method 500a further includes bending the slotted portion of the shaft in at least two spaced apart locations while advancing the catheter through the vasculature of the patient 504a. The method 500b includes advancing an aspiration catheter into a patient distally of an obstruction 502b (e.g., via a guidewire or within an outer catheter or sheath). The aspiration catheter includes a flexible and hollow shaft including a proximal end and a distal end. The shaft includes a slotted portion with a plurality of slotted openings and the slotted portion includes a first segment with a first pattern of slotted openings and a second segment extending proximally relative the first segment with a second pattern of slotted openings different from the first pattern. The method further includes bending the slotted portion of the shaft in at least two spaced apart locations while advancing the catheter through the vasculature of the patient 504b. The method also includes aspirating the obstruction out of the patient through the shaft 506b.

Figure 5C:
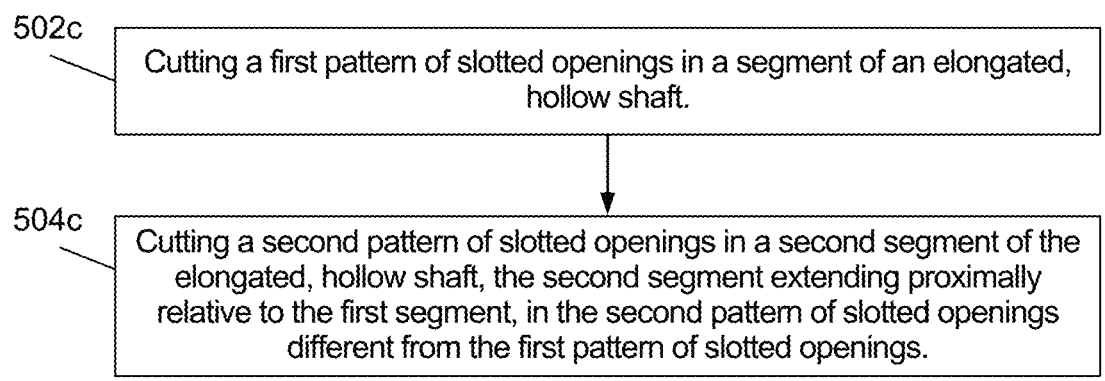
FIG. 5C is a flowchart illustrating an exemplary method of manufacturing a distal access support catheter and/or aspiration catheter in accordance with another aspect of the invention.

FIG. 5C illustrates an exemplary method 500c for manufacturing a distal access support and/or aspiration catheter as described herein. The method 500c includes the steps of cutting a first pattern of slotted openings in a first segment of an elongated, hollow shaft 502c. The method further includes cutting a second pattern of slotted openings in a second segment of the elongated, hollow shaft, the second segment extending proximally relative the first segment, and the second pattern of slotted openings different from the first pattern of slotted openings 504c.

In the description above, various embodiments of the present invention are described. For purposes of explanation, specific configurations and details are set forth in order to provide a thorough understanding of the embodiments. However, it will also be apparent to one skilled in the art that the present invention may be practiced without the specific details. Furthermore, well-known features may be omitted or simplified in order not to obscure the embodiment being described. The subject matter of the present invention is described here with specificity, but the claimed subject matter may be embodied in other ways, may include different, less, or additional elements or steps, and may be used in conjunction with other existing or future technologies.

This description should not be interpreted as implying any particular order or arrangement among or between various steps or elements except when the order of individual steps or arrangement of elements is explicitly described. Different arrangements of the components depicted in the drawings or described above, as well as components and steps not shown or described are possible. Similarly, some features and sub-combinations are useful and may be employed without reference to other features and sub-combinations. Embodiments of the invention have been described for illustrative and not restrictive purposes, and alternative embodiments will become apparent to readers of this patent. Accordingly, the present invention is not limited to the embodiments described above or depicted in the drawings, and various embodiments and modifications may be made without departing from the scope of the claims below.

Other variations are within the spirit of the present invention. Thus, while the invention is susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions, and equivalents falling within the spirit and scope of the invention, as defined in the appended claims.

The use of the terms "a" and "an" and "the" and similar referents in the context of describing the invention (especially in the context of the following claims) are to be construed to cover both the singular and the plural, unless otherwise indicated herein or clearly contradicted by context. The term "or" in reference to a list of two or more items, covers all of the following interpretations of the word: any of the items in the list, all of the items in the list, and any combination of items in the list. The terms "comprising," "having," "including," and "containing" are to be construed as open-ended terms (i.e., meaning "including, but not limited to,") unless otherwise noted. The terms "connected" or "attached" are to be construed as partly or wholly contained within, coupled to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All references, including publications, patent applications, and patents, cited herein are hereby incorporated by reference to the same extent as if each reference were individually and specifically indicated to be incorporated by reference and were set forth in its entirety herein.

What is claimed is:

1. A distal access catheter or shaft configured to be advanced at least partially within a patient, the distal access catheter or shaft comprising:
a flexible and hollow shaft including a proximal end, a distal end, and a lumen there through, the lumen configured to receive an intravascular device configured to be advanced out of the lumen through the distal end of the flexible and hollow shaft, the flexible and hollow shaft including a slotted portion with a plurality of slotted openings, wherein the slotted portion includes a first segment with a first pattern of slotted openings, the first pattern comprising a first slot angle and a first slot spacing, and a second segment extending proximally relative the first segment with a second pattern of slotted openings, the second pattern comprising a second slot angle and a second slot spacing, wherein the second slot angle and the second slot spacing of the second pattern are different from the first slot angle and the first slot spacing of the first pattern.

2. The catheter or shaft of claim 1, wherein the first pattern includes a repeating helical pattern of cut and uncut portions extending circumferentially around and along a length of the first segment, and wherein the second pattern includes a repeating helical pattern of cut and uncut portions extending circumferentially around and along a length of the second segment.

3. The catheter or shaft of claim 2, wherein a longitudinal spacing between the slotted openings of the first pattern at a distal portion of the first segment is smaller relative to a longitudinal spacing between the slotted openings of the second pattern at a proximal portion of the second segment such that a density of the slotted openings at the distal portion is greater relative to a density of the slotted openings at the proximal portion.

4. The catheter or shaft of claim 2, wherein the helical pattern of cut and uncut portions of the first or second patterns extending circumferentially around and along a length of the first or second segments alternates between cut and uncut portions such that uncut portions extend between two cut portions.

5. The catheter or shaft of claim 2, wherein a combined arc length of circumferentially adjacent cut and uncut portions of the helical pattern of the first pattern or second pattern is between 100 degrees and 180 degrees.

6. The catheter or shaft of claim 1, wherein the distal end of the flexible and hollow shaft is coupled to an intravascular device, the intravascular device comprising:
an expandable basket movable between a collapsed configuration and an expanded configuration, the expandable basket configured to be in the collapsed configuration during delivery into a vasculature of the patient via the flexible and hollow shaft and in the expanded configuration during engagement and retrieval of an obstruction, the expandable basket including a proximal end and a distal end, wherein at least one of the proximal end or the distal end is movable relative to each other such that a proximal portion of the expandable basket is invertible towards a distal portion of the expandable basket to form a proximally oriented cavity in the expanded configuration.

7. The catheter or shaft of claim 1, wherein the distal end of the flexible and hollow shaft is coupled to a flow diverter configured to be delivered into a patient's vasculature.

8. The catheter or shaft of claim 1, wherein the distal end of the flexible and hollow shaft is coupled to a coil embolization device configured to be delivered into a patient's vasculature.

9. The catheter or shaft of claim 1, wherein the flexible and hollow shaft is sized and adapted to allow aspiration of an obstruction through the flexible and hollow shaft.

10. The catheter or shaft of claim 1, wherein the flexible and hollow shaft is sized and adapted to allow a delivery catheter for an intravascular device to extend therethrough, the delivery catheter configured to position the intravascular device distally of the distal end of the flexible and hollow shaft.

11. The catheter or shaft of claim 1, wherein the slotted portion is configured to provide the flexible and hollow shaft with flexibility to traverse at least two bends having angles of at least or up to 90 degrees during advancement through the patient.

12. The catheter or shaft of claim 11, wherein the slotted portion is configured to provide the flexible and hollow shaft with flexibility to traverse at least three bends having angles of at least or up to 90 degrees during advancement through the patient.

13. The catheter or shaft of claim 1, wherein a ratio of an area of the slotted portion of the flexible and hollow shaft without slotted openings relative to an area of the slotted portion with slotted openings has a value up to 50%.

14. The catheter or shaft of claim 1, wherein the slotted openings are laser-cut.

15. The catheter or shaft of claim 1, wherein the flexible and hollow shaft further comprises at least one of a non-slotted portion extending proximally relative to the slotted portion or a non-slotted portion extending distally relative to the slotted portion.

16. The catheter or shaft of claim 1, wherein the flexible and hollow shaft comprises a hypotube.

17. The catheter or shaft of claim 1, wherein the flexible and hollow shaft is constructed out of one or more of stainless steel, nitinol, chromium, cobalt, platinum, or polymer.

18. The catheter or shaft of claim 1, wherein the flexible and hollow shaft is operably coupled to or in fluid communication with one or more of a catheter control handle, aspiration source, inflation source, or fluid delivery source.

19. The catheter or shaft of claim 1, wherein the flexible and hollow shaft does not include a coil or braided material.

20. The catheter or shaft of claim 1, further comprising an outer liner extending coaxially around the flexible and hollow shaft.

21. The catheter or shaft of claim 20, wherein the flexible and hollow shaft does not include an inner liner extending coaxially within the flexible and hollow shaft.

22. The catheter or shaft of claim 20, wherein the outer liner has a uniform hardness along its length.

23. The catheter or shaft of claim 22, further comprising an inner liner extending coaxially within the flexible and hollow shaft such that the flexible and hollow shaft is sandwiched between the inner and outer liners.

24. The catheter or shaft of claim 23, wherein the inner liner is directly coupled to the flexible and hollow shaft.

25. A method for positioning a distal access catheter or shaft within a vasculature of a patient, the method comprising:

advancing a distal access catheter or shaft into a patient, the distal access catheter or shaft comprising a flexible and hollow shaft including a proximal end, a distal end, and a lumen there through, the lumen configured to receive an intravascular device configured to be advanced out of the lumen through the distal end of the flexible and hollow shaft, the flexible and hollow shaft including a slotted portion with a plurality of slotted openings, wherein the slotted portion includes a first segment with a first pattern of slotted openings, the first pattern comprising a first pitch and a first longitudinal spacing, and a second segment extending proximally relative the first segment with a second pattern of slotted openings, the second pattern comprising a second pitch and a second longitudinal spacing, wherein the second pitch and the second longitudinal spacing of the second pattern are different from the first pitch and the first longitudinal spacing of the first pattern;

bending the slotted portion of the flexible and hollow shaft in at least two spaced apart locations while advancing the catheter or shaft through the vasculature of the patient; and advancing the intravascular device through the lumen of the distal access catheter or shaft.

26. The catheter or shaft of claim 1, wherein the catheter or shaft is configured to be a distal access support catheter.

27. The catheter or shaft of claim 2, wherein a ratio of an arc length of a cut portion to an arc length of an uncut portion progressively varies along the length of the first or second segment.

28. The catheter or shaft of claim 27, wherein the ratio progressively decreases along the length of the first or second segment.

29. The catheter or shaft of claim 3, wherein the longitudinal spacing of the first or second segment progressively varies along the length of the first or second segment.

30. The catheter or shaft of claim 3, wherein the longitudinal spacing of the first or second segment progressively varies along the length of the first or second segment, and wherein a ratio of an arc length of a cut portion to an arc length of an uncut portion progressively varies along the length of the first or second segment.

31. The catheter or shaft of claim 30, wherein the longitudinal spacing of the first or second segment progressively increases along the length of the first or second segment, and wherein the ratio progressively increases along the length of the first or second segment.

* * * * *